(12) United States Patent
Gruner-Nielsen et al.

(10) Patent No.: US 9,874,519 B2
(45) Date of Patent: Jan. 23, 2018

(54) DISTRIBUTED BRILLOUIN SENSOR

(71) Applicant: OFS Fitel, LLC, Norcross, GA (US)

(72) Inventors: Lars Gruner-Nielsen, Copenhagen (DK); Poul Kristensen, Valby (DK); Tommy Geisler, Brondby (DK)

(73) Assignee: OFS FITEL, LLC, Norcross, GA (US)

( * ) Notice: Subject to any disclaimer, the term of this patent is extended or adjusted under 35 U.S.C. 154(b) by 0 days.

(21) Appl. No.: 14/927,699

(22) Filed: Oct. 30, 2015

(65) Prior Publication Data

US 2017/0153178 A1 Jun. 1, 2017

Related U.S. Application Data

(60) Provisional application No. 62/074,201, filed on Nov. 3, 2014, provisional application No. 62/133,627, filed on Mar. 16, 2015.

(51) Int. Cl.
*G01N 21/63* (2006.01)
*G02B 6/02* (2006.01)
*G02B 6/036* (2006.01)

(52) U.S. Cl.
CPC ....... *G01N 21/636* (2013.01); *G02B 6/02028* (2013.01); *G02B 6/02252* (2013.01); *G02B 6/03644* (2013.01); *G01N 2021/638* (2013.01)

(58) Field of Classification Search
CPC .......... G01N 21/636; G01N 2021/638; G02B 6/02028; G02B 6/02252; G02B 6/03644
See application file for complete search history.

(56) References Cited

U.S. PATENT DOCUMENTS

2013/0341497 A1* 12/2013 Zuardy ............. G01D 5/35358
250/227.14

* cited by examiner

*Primary Examiner* — David Porta
*Assistant Examiner* — Faye Boosalis

(57) ABSTRACT

A distributed Brillouin sensor system comprising a pump laser, a Brillouin sensor fiber, and a detector system is described. The pump laser is arranged so as to send a pump signal into a first end of the Brillouin sensor fiber, and the detector system is arranged to detect Brillouin backscattering from the Brillouin sensor fiber. The Brillouin sensor fiber is characterized by having a negative dispersion, and further by an effective area of the sensor fiber being less than or equal to 50 μm².

17 Claims, 3 Drawing Sheets

DISTRIBUTED BRILLOUIN SENSOR

CROSS REFERENCE TO RELATED APPLICATIONS

The present patent application is related and claims priority to provisional U.S. application Ser. No. 62/074,021 filed on Nov. 3, 2014, and provisional U.S. application No. 62/133,627 filed on Mar. 16, 2015, the entire contents of which are incorporated here in by reference.

TECHNICAL FIELD

The present invention relates to a distributed Brillouin sensor system. The invention further relates to a use of a Brillouin sensor fiber or a fiber assembly for use in a distributed Brillouin sensor system.

BACKGROUND

Optical fibers are often used for communication purposes, where light waves can propagate in the fiber over long distances with low or no loss. However, by enhancing the sensitivity of the light properties to environmental influences, the optical fibers can be used to detect or monitor external perturbations, such as temperature or stress.

Such optical fiber sensors can be implemented as point sensors, where only one location along the optical fiber is made sensitive to the external perturbations. Accordingly, one optical fiber is needed per point, which is to be monitored. Alternatively, the fiber optical sensors can be implemented as distributed sensors, where the optical fiber is a long uninterrupted linear sensor.

When the power of the propagated light exceeds a given threshold, non-linear phenomena, such as Brillouin scattering starts to occur. Due to its strong dependence on the aforementioned environmental variables, Brillouin scattering is often employed in distributed optical fiber sensor systems.

Brillouin scattering occurs due to the interaction between an electromagnetic wave and matter, which can generate variations in the molecular structure of the material. The incident light wave generates acoustic waves and induces a periodic modulation of the refractive index, which in turn forms a light-backscattering similar to a Bragg grating. The scattered light is down-shifted in frequency due to the Doppler shift associated with the grating moving at the acoustic velocity. The acoustic velocity is dependent on the density of the material. The density of the material is temperature-dependent as a result of thermal expansion so that a peak frequency of the interaction is observed to change with temperature. Further, any deformation experienced by the fiber will also have an impact on the density of the material, whereby the fiber can be used as a distributed strain gauge by observing a shift when the fiber is elongated.

By using different time domain or frequency correlation techniques, the Brillouin shift process can accurately be located along the optical fiber.

C. A. Galindez-Jemioy and J. M. López-Higuera, "Brillouin Distributed Fiber Sensors: An Overview and Applications", Journal of Sensors, Volume 2012 is a review article that provides an overview and applications of various Brillouin sensor setups, which are incorporated in the present invention by reference.

Luc Thévenaz, "Brillouin distributed time-domain sensing in optical fibers: state of the art and perspectives", Front. Optoelectron. China, Higher Education Press and Springer Verlag Berlin Heidelberg, 2010 is another review article that provides an overview and applications of various Brillouin sensor setups, which are incorporated in the present invention by reference.

The Brillouin based sensor systems today utilize standard single-mode fibers. However, such fibers are attributed with a poor Brillouin gain coefficient and unwanted nonlinear effects that may cause modulation instability. Accordingly, there is a need for improved distributed Brillouin sensor systems.

SUMMARY OF THE INVENTION

An object of the invention is to provide an improved distributed Brillouin sensor system A further object of the invention is to provide a distributed Brillouin sensor system having a tailored Brillouin sensor fiber.

An additional object of the invention is to provide the use of a tailored Brillouin sensor fiber for a Brillouin sensor system.

A further object of the invention is to provide a Brillouin sensor system that allows for temperature or strain sensing at a farther distance than existing Brillouin sensor systems.

According to a first aspect, the invention provides a distributed Brillouin sensor system comprising a pump laser, a Brillouin sensor fiber, and a detector system, wherein
  the pump laser is arranged so as to send a pump signal into a first end of the Brillouin sensor fiber, and
  the detector system is arranged to detect Brillouin backscattering from the Brillouin sensor fiber, wherein the Brillouin sensor fiber is characterized by having
    a negative dispersion, and wherein
    an effective area of the Brillouin sensor fiber is less than or equal to 50 µm$^2$.

By utilizing a Brillouin sensor fiber having a negative dispersion it is possible to lower the effective area of the fiber without seriously affecting nonlinear effects such as modulation instability, thereby in effect increasing the Brillouin gain of the optical fiber for a given pump power.

In a first embodiment, the sensor system further comprises a probe laser arranged so as provide a probe signal into an opposite end of the Brillouin sensor fiber. Such a setup leads to a more efficient scattering efficiency. However, the invention also contemplates that the Brillouin sensor system may be based on a spontaneous Brillouin sensor system or a backscattering Brillouin sensor system.

In one embodiment, an effective area of the sensor fiber is less than or equal to 60 µm$^2$. The effective area of the sensor fiber may also be less than or equal to 50 µm$^2$. The effective area of the sensor fiber may even be less than or equal to 40 µm$^2$. The relative small effective area increases the Brillouin gain but would normally lead to unwanted non-linear effects such as modulation instability. However, the negative dispersion of the fiber compensates for this.

The effective area of the sensor fiber may for instance be in the interval from 10 to 50 µm$^2$. The effective area of the sensor fiber may advantageously be in the interval from 15 to 35 µm$^2$, which has shown to provide excellent properties for the Brillouin sensor fiber.

In another embodiment, the Brillouin sensor fiber is further characterized by having a low attenuation, and a high Brillouin gain.

The attenuation may for instance be 0.25 dB/km or less. The attenuation may for instance be 0.24 dB/km or less. The attenuation may for instance be 0.23 dB/km or less. The attenuation may for instance be 0.22 dB/km or less. The attenuation may for instance be 0.21 dB/km or less. The attenuation may for instance be 0.20 dB/km or less.

In one advantageous embodiment, the dispersion is more negative than −2 ps/nm/km, advantageously more negative than −5 ps/nm/km.

The Brillouin gain may advantageously be at least twice the Brillouin gain of a G.652 standard single-mode fiber.

In one embodiment, the Brillouin sensor fiber comprises a central core region having a maximum refractive index, $n_1$, and a layer of transparent cladding material on the outer surface of said glass fiber having a nominal refractive index of $n_2$, wherein $0.003 < n_1 - n_2 < 0.015$ and wherein the glass fiber includes a first annular region of transparent material adjacent to the central core region, said first annular region having a width of about 1-10 micrometers and a refractive index, $n_3$, wherein $-0.01 < n_3 - n_2 \leq 0$; and the glass fiber further includes a second annular region of transparent material adjacent to the outer cladding whose refractive index is $n_4$, wherein $0 \leq n_4 - n_2 < 0.015$ The refractive index $n_2$ of the cladding may for instance be 1.457 @633 nm and can be used as a reference. The above values may also be converted to relative values by dividing by the value of $n_2$, i.e. advantageously by dividing by 1.457.

The Brillouin sensor fiber may advantageously exhibit the mentioned characteristics for all wavelengths in the region 1530-1565 nm.

The pump signal is preferably composed of optical pulses. The probe signal may advantageously be composed of continuous wave light.

The Brillouin sensor may have a length of at least 5 km, advantageously at least 10 km.

According to an additional first aspect, the invention provides a use of a sensor fiber for a Brillouin sensor fiber system, wherein the sensor fiber has a negative dispersion.

The invention additionally provides a use of a sensor fiber for a Brillouin sensor system, wherein the sensor fiber comprises a central core region having a maximum refractive index, $n_1$, and a layer of transparent cladding material on the outer surface of said glass fiber having a nominal refractive index of $n_2$, wherein $0.003 < n_1 - n_2 < 0.015$ and wherein the glass fiber includes a first annular region of transparent material adjacent to the central core region, said first annular region having a width of about 1-10 micrometers and a refractive index, $n_3$, wherein $-0.01 < n_3 - n_2 \leq 0$; and the glass fiber further includes a second annular region of transparent material adjacent to the outer cladding whose refractive index is $n_4$, wherein $0 \leq n_4 - n_2 < 0.015$.

As previously mentioned, an effective area of the sensor fiber is less than or equal to 50 µm², e.g. in the range 15-35 µm².

According to a second aspect, the invention provides a distributed Brillouin sensor system comprising a pump laser, and a combined fiber assembly including at least a first optical fiber section and a second optical fiber section, wherein the pump laser is arranged so as to send a pump signal into a first end of combined fiber assembly, and the detector system is arranged to detect Brillouin backscattering from the combined fiber assembly, wherein the combined fiber assembly is characterized by the first section having a low Brillouin gain and the second fiber section having a high Brillouin gain.

Accordingly, it is seen that the first section may guide light without suffering from non-linear penalties associated with a high Brillouin gain fiber, whereas the second fiber section after the light is attenuated by the first section have a high Brillouin gain without any non-linear penalties. This may significantly extend the reach of the distributed Brillouin sensor system.

It is recognized that the combined fiber assembly may comprise a plurality of first fiber sections and second fiber sections.

It is also recognized that the second fiber section may comprise any of the characteristics described in the aforementioned embodiments described for the first aspect.

In a first embodiment, the sensor system further comprises a probe laser arranged so as provide a probe signal into an opposite end of the Brillouin sensor fiber. Such a setup leads to a more efficient scattering efficiency. However, the invention also contemplates that the Brillouin sensor system may be based on a spontaneous Brillouin sensor system or a backscattering Brillouin sensor system.

In one advantageous embodiment, the Brillouin gain of the second fiber section is at least 2.0 times larger than the Brillouin gain of the first fiber section.

In another advantageous embodiment, the first fiber section has a first effective area, and the second fiber section has a second effective area, and wherein the first effective area is at least 1.5 and advantageously at least 2.0 times larger than the second effective area. The effective area of the first section may for instance be equal to or greater than 100 µm².

The attenuation of the first fiber section may advantageously be equal to or less than 0.175 dB/km.

In a highly advantageous embodiment, a reach of the distributed Brillouin sensor system is increased by at least 10 km by use of the combined fiber assembly.

The first fiber section may advantageously be characterized by having a positive dispersion. However, the second fiber section may alternatively have a negative dispersion.

BRIEF DESCRIPTION OF THE DRAWINGS

The invention is explained in detail below with reference to the drawing(s), in which.

DETAILED DESCRIPTION OF THE INVENTION

Figure 1:
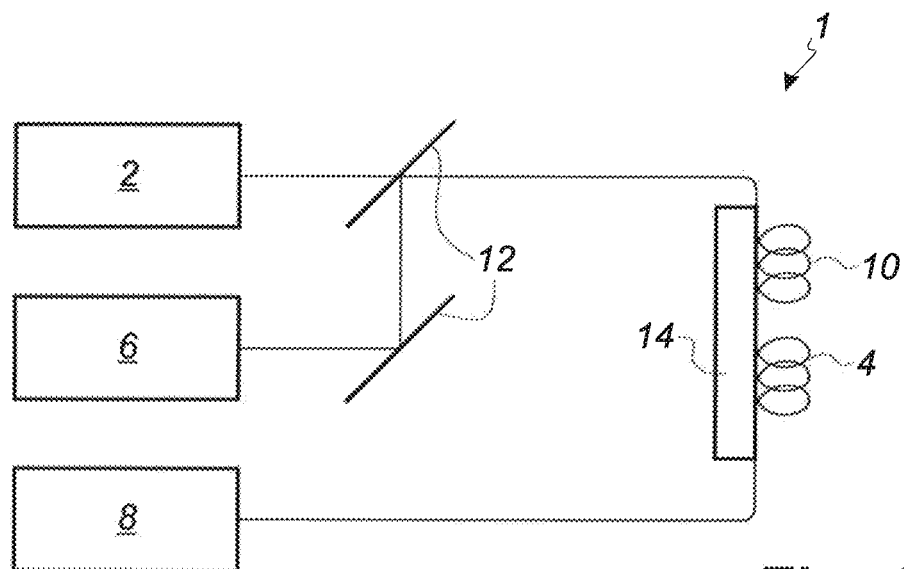
FIG. 1 shows a schematic drawing of a distributed Brillouin sensor system according to the invention.

FIG. 1 shows a Brillouin sensor system 1 according to the invention. The Brillouin sensor system 1 shown utilizes stimulated Brillouin scattering, which is achieved by using an optical pulse, called the pump, and a continuous wave called the probe signal, which is used to probe the Brillouin frequency profile of the fiber.

The Brillouin sensor system 1 comprises a pump laser 2, which sends the optical pulse into an optical fiber assembly. The optical fiber assembly comprises an optional first fiber section 10 and a second fiber section 4 in form of a Brillouin sensor fiber according to the invention. The two fiber sections are coupled in series such that the emitted optical pulse from the pump laser 2 is emitted into a first end of the first fiber section 10 and sent to the Brillouin sensor fiber 4.

The two fiber sections 10, 4 are advantageously configured to be attached to a structure 14 to be sensed for strain and temperature distribution. The structure 14 may for instance be a bridge or a pipe line or another long object.

The Brillouin sensor system 1 further comprises a probe laser 8, which emits the probe signal into a first end of the additional first fiber section 10 and in an opposite direction of the optical pulse. Backscattered light from the system 1 is sent to a detector system 6, e.g. in form of an interrogator. The backscattered light may for instance be sent to the detector system 6 via a beam splitter setup 12. The probe laser 8 may advantageously produce a continuous wave tunable probe signal.

The pump laser 2, the detector setup 6, and the probe laser 8 may be integrated in a single unit or a plurality of single units.

A stimulation of the Brillouin scattering process occurs when the frequency difference between the optical pulse and the probe signal corresponds to the Brillouin shift and provided that the two signals are counter-propagating in the fiber. The interaction between the two signals leads to a larger scattering efficiency, resulting in an energy transfer from the pulse signal to the probe signal and an amplification to the probe signal.

Distributed sensing is based on the analysis of backscattered light emitted when the optical pulse is transmitted to the Brillouin sensor fiber 4. The backscattering occurs due to interaction of light with density fluctuations and molecular vibrations of the propagation medium of the Brillouin sensor fiber 4. Spontaneous backscattering occurs at every point of the Brillouin sensor fiber 4, thus enabling a distributed sensor setup via a single optical fiber.

Figure 2:
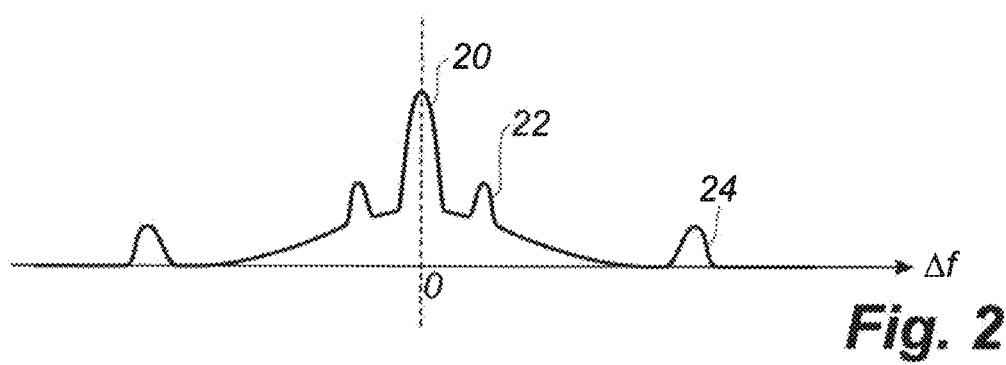
FIG. 2 illustrates a spectrum of backscattered light from a laser source propagating in an optical fiber.

A typical backscattering spectrum is shown in FIG. 2. The backscattering is broken up into Stokes and anti-stokes components which form a symmetric pattern around $\Delta f = 0$. Rayleigh scattering 20 produces the largest degree of backscattering and is located at the same frequency as the pump laser 2. Brillouin scattering 22 produces backscattering at a lower intensity than Rayleigh scattering due to thermally excited acoustic waves or phonons. The Brillouin scattering exhibits a frequency shift of approximately 10 GHz corresponding to 0.1 nm at a wavelength of 1550 nm. As later explained the frequency shift is directly related to both local temperature and strain conditions of the Brillouin sensor fiber 4. Thereby, a distributed temperature and/or strain sensor system may be obtained. Further, as already explained, Brillouin scattering can be stimulated, thereby increasing the magnitude of backscattering and making it suitable for sensing over large distances. Raman scattering 24 produces backscattering at the lowest intensity due to thermally excited molecular vibrations and exhibits a frequency shift of up to 13 THz or 100 nm at a wavelength of 1550 nm.

Figure 3:
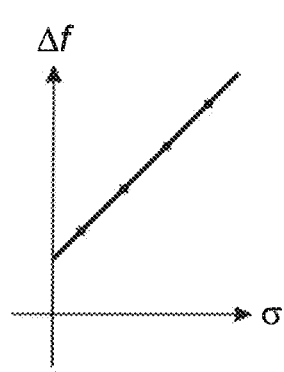
FIGS. 3 and 4 illustrate Brillouin frequency shift as a function of strain and temperature, respectively.
Figure 4:
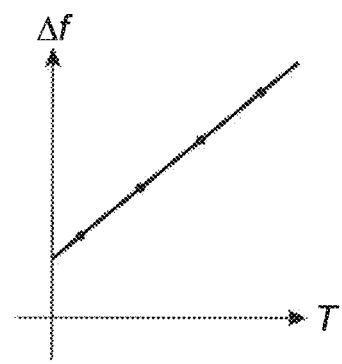

The Brillouin scattering occurs due to the interaction between the optical pulse from the pump laser 2 and matter of the Brillouin sensor fiber 4, which can generate variations in the molecular structure of the material of the Brillouin sensor fiber 4. The incident light wave generates acoustic waves and induces a periodic modulation of the refractive index, which in turn forms a light-backscattering similar to a Bragg grating. The scattered light is down-shifted in frequency due to the Doppler shift associated with the grating moving at the acoustic velocity. The acoustic velocity is dependent on the density of the material. The density of the material in turn is temperature-dependent as a result of thermal expansion so that a peak frequency of the interaction is observed to change with temperature. Further, any deformation experienced by the fiber will also have an impact on the density of the material, whereby the fiber can be used as a distributed strain gauge by observing a shift when the fiber is elongated. As shown in FIG. 3, the detected frequency shift $\Delta f$ is substantially linear dependent on strain a. Further, as shown in FIG. 4, the detected frequency shift $\Delta f$ is also substantially linear dependent on temperature T. An optical fiber may be configured so that it is dedicated to probe either stress, temperature, or both stress and temperature. This may for instance be achieved by having a first optical fiber, which is attached to the structure, whereby stresses from the structure will result in an elongation of the fiber and hence a Brillouin shift. Similarly, another optical fiber may be arranged in a tube, such that the fiber is not affected by the stresses in the structure and hence be dedicated to detect temperature only.

Figure 5:
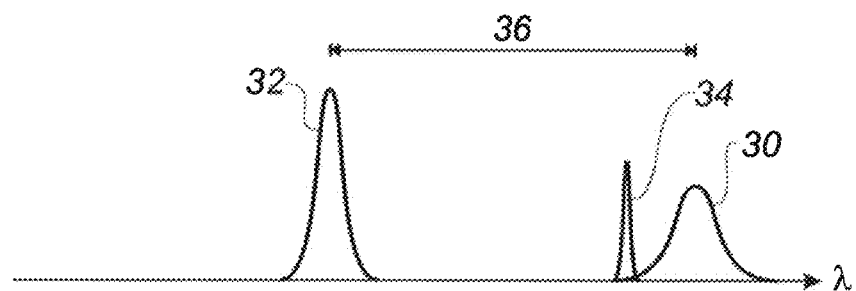
FIG. 5 illustrates the wavelength distribution of the pump pulse, the Brillouin gain associated with the pump pulse, and the probe signal.

As mentioned the optical pulse from the pump laser 2 enters the fiber assembly from, one end, and the light from the probe laser 8 enters the fiber assembly from the opposite end. The two signals interact through stimulated Brillouin scattering when a resonance frequency condition is met. The interaction between the two signals is maximized the frequency difference between the pump laser 2 and the probe laser 8 matches the local Brillouin frequency shift. This is illustrated in FIG. 5, which shows a wavelength of a pump pulse 32 and a Brillouin gain 30 associated with the pump pulse 30. Further, the wavelength of a probe 34, which is tunable such that the wavelength of the probe 34 may be scanned to match a Brillouin shift 36. Accordingly, the probe can accurately locate the Brillouin shift, which is directly related to stress and/or temperature.

The probe signal 34 carries information about an event in form of local temperature and strain as well as the location for processing. Since the pump signal 32 is an optical pulse, the probe signal 34 carries time domain information, which can be converted to a distance based on the known speed of light in the fiber assembly. Scanning the pump and probe frequency difference using the tunable probe signal 34 thus allows to determine the Brillouin frequency shift at every location along the fiber assembly.

Figure 6:
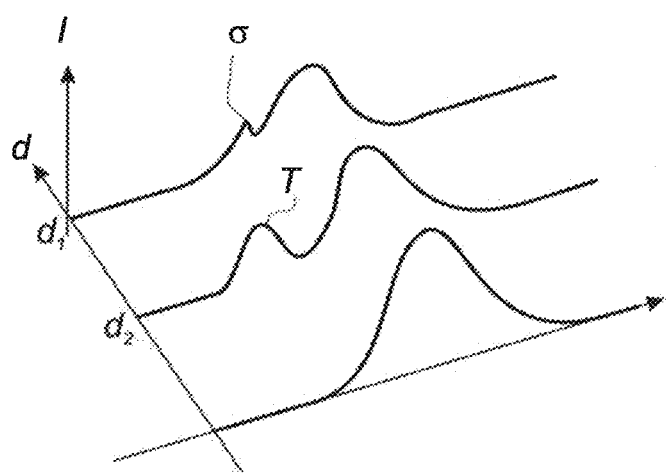
FIG. 6 illustrates a waterfall plot for detected Brillouin spectrums as a function of distance and frequency.

Measurement scans may thereby be detected along the length of the fiber assembly and depicted as a 3D graph, e.g. as a waterfall plot as shown in FIG. 6. A local stress incidence may for instance be detected with a dedicated strain sensing fiber at a distance $d_1$, and a local temperature incidence may for instance be detected with a dedicated temperature sensing fiber at a distance $d_2$.

The Brillouin gain is proportional to the ration $P_P \cdot g_B / A_{eff}$, where $P_P$ is the pump power, $g_B$ is the Brillouin gain coefficient of the fiber, and $A_{eff}$ is the effective area of the fiber. $g_B$ is governed by the overlap integral between the optical field and the acoustic phonons responsible for the Brillouin scattering; that is $g_B$ will depend of the refractive as well as the acoustic index profile both governed by the doping distributions. Decreasing the effective area will increase the Brillouin gain; however, it will also increase the non-linear coefficient $\gamma$, which is proportional to $n_{nl}/A_{eff}$, where $n_{nl}$ is the nonlinear refractive index, which depend of the fiber refractive index and doping distributions. Nonlinear effects such as modulation instability will depend on $\gamma \cdot P_P$.

A distributed Brillouin gain has experimentally been compared by to exponential decay equivalent of the fiber attenuation for a standard single-mode fiber (G.652). The gain of the standard single-mode fiber follows an exponential decay of 0.19 dB/km fiber loss.

Similarly, an experiment was carried out for an optical fiber having a smaller effective area than the standard single-mode fiber (approximately ⅓ of the effective area of the standard single-mode fiber) and for the same pump power. The experiments showed that the Brillouin gain decays more rapidly than an exponential corresponding to fiber loss of 0.28 dB/km. The experiments showed that in order for the Brillouin gain to follow an exponential decay, the pump power has to be decreased by 4 dB, whereby the Brillouin gain follows an exponential fiber loss of 0.28 dB/km.

It was observed that the Brillouin gain for the modified fiber relative to standard single-mode fiber is increased from 4% to 9.3%, i.e. a factor 2.3 in the beginning of the fiber. However, the Brillouin gain decreases rapidly with length attributed to modulation instability. The modulation instability is due to the smaller effective area of the modified fiber relative to the standard single-mode fiber and thereby higher nonlinear coefficient. To get rid of modulation instability, it is necessary to decrease the pump power by 4 dB.

It was further observed that for length of up to 5 km, the modified fiber shows a small advantage. However, for distances above 5 km, the standard single-mode fiber is superior due to its lower attenuation. Clearly, this shows that there is a need for new fiber designs that are dedicated for Brillouin sensing.

In order to demonstrate the invention, a dedicated Brillouin sensor fiber according to the invention was compared with a standard single-mode fiber (0.652). The dedicated Brillouin sensor fiber is characterized by having a smaller effective area (approximately ⅓ of that of the standard single-mode fiber) but further being characterized by having a negative dispersion.

It was observed that the Brillouin gain for the dedicated Brillouin sensor fiber relative to the standard single-mode fiber is increased from 4.5% to 8%, i.e. a factor 1.8 at the proximal end of the fiber. As the same pump power was used for both fibers, it can be concluded that the Brillouin gain coefficient is a factor 1.8 higher in the dedicated Brillouin sensor fiber relative to the standard single-mode fiber.

In contrast to the afore-mentioned modified optical fiber, no sign of modulation instability was observed for the dedicated Brillouin sensor fiber even though the effective areas and thereby the nonlinear coefficient is almost identical between the two. This is attributed to the fact that the dedicated Brillouin sensor fiber has a negative dispersion coefficient (normal dispersion) in contrary to the modified fiber, which has a positive dispersion coefficient (anomalous dispersion). Modulation instability can only occur if the dispersion is anomalous. It is observed that even out to 48 km the dedicated Brillouin sensor fiber shows a higher Brillouin gain than the standard single-mode fiber, but due to the higher loss of the dedicated Brillouin sensor fiber, the advantage becomes smaller for distances above ~20 km.

From the above, some general conclusions can be drawn:
1. Increased Brillouin gain is helpful, but it only helps at long distances if the attenuation is low as well.
2. For fibers with anomalous dispersion the maximum pump power is determined by modulation instability. To avoid modulations instability in the anomalous dispersion regime the ratio $P_P \cdot g/A_{eff}$ should be below a certain threshold.
3. Fiber with normal dispersion can tolerate at much higher $P_P \cdot \gamma/A_{eff}$ ratio than fibers with anomalous dispersion without penalties.

From this, it can be concluded that an optimum fiber for distributed Brillouin sensing is characterized by:
1. Low loss. Preferable around 0.25 dB/km or lower.
2. Negative dispersion
3. High Brillouin gain The high Brillouin gain is especially important if pump power is limited.

Table 1 shows three examples of Brillouin sensor fibers according to the invention which provide improved sensing performance than existing Brillouin sensor systems.

TABLE 1

Examples of Brillouin sensor fibers compared to a standard single-mode fiber @ 1550 nm.

| Fiber | Attenuation [dB/km] | Effective Area [µm²] | $g_B/A_{eff}$ Rel. to SSMF | Dispersion [ps/(nm · km)] |
|---|---|---|---|---|
| Standard single-mode fiber (SSMF) | 0.19 | 82 | 1 | 17 |
| Example I | 0.21 | 32 | 2.0 | −2.5 |
| Example II | 0.23 | 23 | 2.9 | −27 |
| Example III | 0.24 | 22 | 3.7 | −6 |

It is seen that the three examples all have relative low attenuation, a small effective area compared to a standard single-mode fiber, a relative high Brillouin gain, and a negative dispersion. Overall, the optical fibers according to Examples I-III have shown to make it possible to extend the sensing reach with more than 10 km compared to a standard single-mode optical fiber.

Figure 7A:
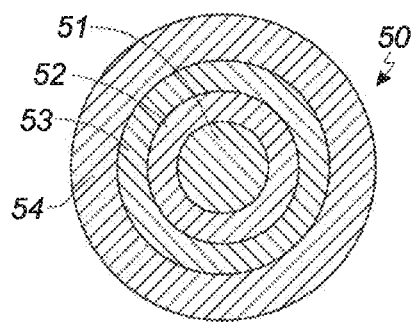
FIGS. 7A and 7B show a cross section and a refractive-index profile of a Brillouin sensor fiber according to the invention, respectively.
Figure 7B:
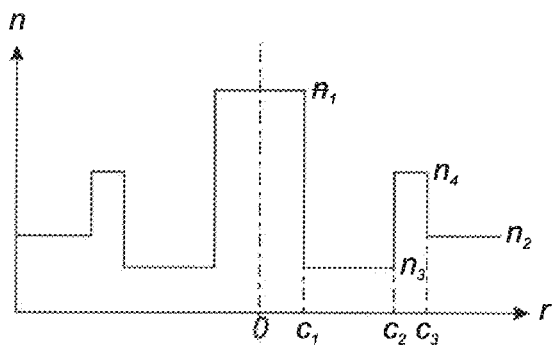

FIG. 7A illustrates a cross section of an optical fiber 50, which exhibits the desired characteristics for the dedicated Brillouin sensor fiber 4. The optical fiber 50 is an un-coated glass fiber having a plurality of layers 51-54, each having a different index of refraction for modifying the waveguide dispersion characteristic of the fiber. FIG. 7A suggests that changes in refractive index are abrupt between layers, although this is not necessarily the case. Gradual index changes are more common and such fibers are known as graded index fibers. Nevertheless, to facilitate an understanding of the present invention, abrupt changes are shown. It is understood that the present invention contemplates graded index fibers also.

The optical fiber 50 comprises a central core region 51 whose index of refraction is nominally $n_1$. The central core region 51 is surrounded by a first annular ring 52 of nominal refractive index $n_3$, which in turn is surrounded by a second annular ring 53 of nominal refractive index $n_4$. An outer cladding 54 of nominal refractive index $n_2$ surrounds the second annular ring 53. It is noted that the drawing of FIG.

7A is not to scale since the diameter of cladding layer 54 is about 125 microns, while the diameter of the central core 51 is about 8 microns.

The refractive indices are defined as follows:

$$0.003 < n_1 - n_2 < 0.015;$$

$$-0.01 < n_3 - n_2 \le 0; \text{ and}$$

$$0 \le n_4 - n_2 < 0.015.$$

The refractive index of the cladding 54 may approximately be 1.457 @633 nm. The above values for the difference in refractive index may also be converted to percentage by dividing by 1.457. From the above intervals, it is recognized that the optical fiber 50 also may have only a single annular ring or two annular rings surrounding the central core 50.

The radiuses $c_1$, $c_2$, $c_3$ of the three layers 51-53 may advantageously be as follows:

$$2.0 \text{ }\mu\text{m} \le c_1 \le 30 \text{ }\mu\text{m}$$

$$0 < c_2 \le 10 \text{ }\mu\text{m}$$

$$0 < c_3 \le 10 \text{ }\mu\text{m}$$

However, according to the invention, it is possible to extend the reach of the Brillouin sensor system 1 even further by utilizing a fiber assembly according to the invention, in particular by using a first fiber section 10 with a relative low Brillouin gain and a Brillouin sensor fiber 4 having a relative high gain. It is noted that the Brillouin sensor fiber 4 may advantageously be a dedicated Brillouin sensor fiber according to the invention, e.g. as specified in Examples I-III. However, the reach of existing Brillouin sensor systems may also be extended by utilizing a first fiber section with a relative low Brillouin gain, e.g. by combining such an optical fiber with a standard single-mode fiber used for Brillouin sensing having a positive dispersion. In the following, however, this aspect of the invention will be explained in combination with a dedicated Brillouin sensor fiber according to Example II.

The first fiber section 10 may advantageously comprise an pure silica core fiber exhibiting the characteristics as shown in Table 2.

TABLE 2

Examples of optical fiber for first fiber section of a fiber assembly according to the invention @ 1550 nm.

| Fiber | Attenuation [dB/km] | Effective Area [µm²] | $g_B/A_{eff}$ Rel. to SSMF | Dispersion [ps/(nm · km)] |
|---|---|---|---|---|
| Example A | 0.170 | 82 | ~1 | 19 |
| Example B | 0.167 | 153 | ~0.55 | 21 |

Figure 8A:
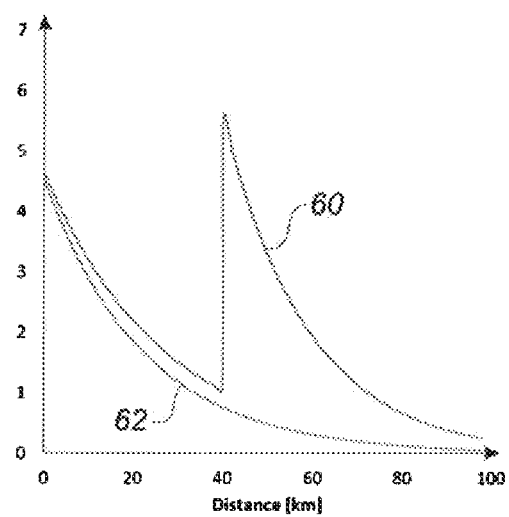
FIGS. 8A and 8B illustrate a power of a Brillouin signal for a fiber assembly according to the invention.
Figure 8B:
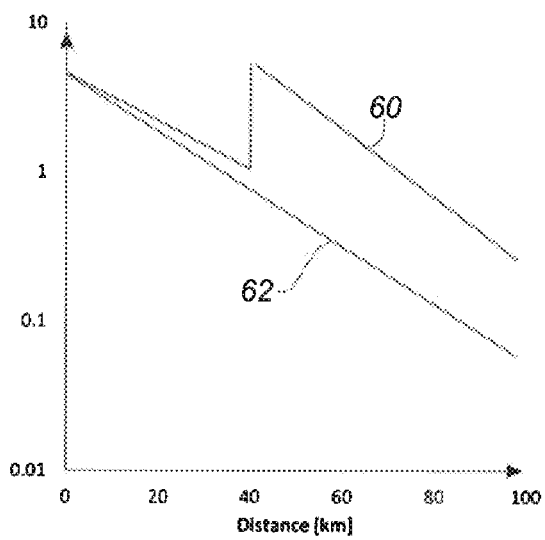

An example of an obtainable performance for a fiber assembly according to the invention is shown in FIG. 8A showing Brillouin signals in arbitrary unit on a linear scale as a function of distance and FIG. 8B showing the Brillouin signals in arbitrary unit on a logarithmic scale as a function of distance. The graphs show the characteristics 60 for a fiber assembly according to the invention compared to the characteristics 62 a standard single-mode fiber (G.652).

The fiber assembly comprises a first fiber section 10 according to Example B having a length of 40 km and a Brillouin sensor fiber 4 according to Example II having a length of 60 km.

In the two cases, the input power has been adjusted such that the power over effective area is kept the same. The advantage of this combination is that the fiber with low Brillouin gain, i.e. the first fiber section 10, typical will have a high effective area meaning that it can accept more power before performance is degraded by other non-linearities such as Raman scattering. When the power reach the high Brillouin gain fiber, i.e. the second fiber section 4, which typical have a low effective area and therefore can only accept lower power, the power is already attenuated by the first fiber section 10.

It is seen by such a combination of fibers much larger reach improvement can be obtained than with a single fiber. In the example of FIGS. 8A and 8B, the reach can be improved from −50 km to −85 km.

In the example shown in FIGS. 8A and 8B, the first fiber section 10 has a positive dispersion, but it should be appreciated that negative dispersion for the first section 10 might also be a possibility. It should also be appreciated that more than two different fibers e.g. three or four might yield even better performance.

While the setup has been explained in relation to a stimulated Brillouin sensor setup, it is recognized that the invention also contemplates the use of a spontaneous Brillouin sensor setup.

REFERENCE NUMERALS

| | |
|---|---|
| 1 | Distributed Brillouin sensor system |
| 2 | Pump laser |
| 4 | Brillouin sensor fiber/second fiber section |
| 6 | Detector system/detector/interrogator |
| 8 | Probe laser |
| 10 | First fiber section |
| 12 | Splitter |
| 14 | Structure |
| 20 | Rayleigh scattering |
| 22 | Brillouin scattering |
| 24 | Raman scattering |
| 30 | Brillouin gain spectrum |
| 32 | Pump pulse |
| 34 | Probe |
| 36 | Brillouin shift |
| 50 | Optical fiber |
| 51-54 | Layers of optical fiber |
| 60 | Brillouin signal for a fiber assembly according to the invention |
| 62 | Brillouin signal for a standard single-mode fiber |
| d | distance |
| f | frequency |
| Δf | Brillouin shift |
| T | Temperature |
| λ | Wavelength |
| σ | Strain |

What is claimed is:

1. A distributed Brillouin sensor system comprising a pump laser, a Brillouin sensor fiber, and a detector system, wherein
   the pump laser is arranged so as to send a pump signal into a first end of the Brillouin sensor fiber, and
   the detector system is arranged to detect Brillouin backscattering from the Brillouin sensor fiber, wherein the Brillouin sensor fiber is characterized by having
   a negative dispersion, and wherein
   an effective area of the sensor fiber is less than or equal to 50 µm².

2. The distributed Brillouin sensor system according to claim 1, wherein the sensor system further comprises a probe laser arranged so as provide a probe signal into an opposite end of the Brillouin sensor fiber.

3. The distributed Brillouin sensor according to claim 2, wherein the probe signal is composed of continuous wave light.

4. The distributed Brillouin sensor system according to claim 1, wherein the Brillouin sensor fiber is further characterized by having
a low attenuation, and
a high Brillouin gain.

5. The distributed Brillouin sensor system according to claim 4, wherein the attenuation is less than 0.25 dB/km.

6. The distributed Brillouin sensor system according to claim 4, wherein the attenuation is less than 0.20 dB/km.

7. The distributed Brillouin sensor system according to claim 4, wherein the Brillouin gain is at least twice the Brillouin gain of a G.652 standard single-mode fiber.

8. The distributed Brillouin sensor system according to claim 1, wherein the dispersion is more negative than −2 ps/nm/km, advantageously more negative than −5 ps/nm/km.

9. The distributed Brillouin sensor system according to claim 1, wherein the Brillouin sensor fiber comprises a central core region having a maximum refractive index, $n_1$, and a layer of transparent cladding material on the outer surface of said glass fiber having a nominal refractive index of $n_2$, wherein $0.003 < n_1 - n_2 < 0.015$ and wherein the glass fiber includes a first annular region of transparent material adjacent to the central core region, said first annular region having a width of about 1-10 micrometers and a refractive index, $n_3$, wherein $0.01 < n_3 - n_2 \leq 0$; and the glass fiber further includes a second annular region of transparent material adjacent to the outer cladding whose refractive index is $n_4$, wherein $0 \leq n_4 - n_2 < 0.015$.

10. The distributed Brillouin sensor system according to claim 9, wherein the central core comprises three annular regions having radii $c_1$, $c_2$, and $c_3$, wherein $2.0\ \mu m \leq c_1 \leq 3.0\ \mu m$ $0 < c_2 \leq 10\ \mu m$ $0 < c_3 \leq 10\ \mu m$.

11. The distributed Brillouin sensor system according to claim 1, wherein the Brillouin sensor fiber exhibits the mentioned characteristics for all wavelengths in the region 1530-1565 nm.

12. The distributed Brillouin sensor system according to claim 1, wherein the pump signal is composed of optical pulses.

13. The distributed Brillouin sensor according to claim 1, wherein the Brillouin sensor fiber has a length of at least 5 km, advantageously at least 10 km.

14. Use of a sensor fiber for a Brillouin sensor fiber system, wherein the sensor fiber has a negative dispersion, comprising the steps of:
sending a pump signal into a first end of the sensor fiber; and
detecting Brillouin backscattering from the sensor fiber.

15. Use of a sensor fiber according to claim 14, wherein an effective area of the sensor fiber is less than or equal to 50 $\mu m^2$.

16. Use of a sensor fiber for a Brillouin sensor system, wherein the sensor fiber comprises a central core region having a maximum refractive index, $n_1$, and a layer of transparent cladding material on the outer surface of said glass fiber having a nominal refractive index of $n_2$, wherein $0.003 < n_1 - n_2 < 0.015$ and wherein the glass fiber includes a first annular region of transparent material adjacent to the central core region, said first annular region having a width of about 1-10 micrometers and a refractive index, $n_3$, wherein $0.01 < n_3 - n_2 \leq 0$; and the glass fiber further includes a second annular region of transparent material adjacent to the outer cladding whose refractive index is $n_4$, wherein $0 \leq n_4 - n_2 < 0.015$, wherein the use of the sensor fiber comprises the steps of:
sending a pump signal into a first end of the sensor fiber; and
detecting Brillouin backscattering from the sensor fiber.

17. Use of a sensor fiber according to claim 16, wherein an effective area of the sensor fiber is less than or equal to 50 $\mu m^2$.

* * * * *